US00PP22458P3

(12) United States Plant Patent
Holland et al.

(10) Patent No.: US PP22,458 P3
(45) Date of Patent: Jan. 17, 2012

(54) ALMOND TREE NAMED 'MATAN'

(50) Latin Name: *Prunus dulcis*
Varietal Denomination: Matan

(75) Inventors: Doron Holland, Hasolelim (IL); Irit Bar-Ya'akov, Qiryat Tivon (IL); Kamel Hatib, Arrabe (IL); Reuven Birger, Kfar Kish (IL)

(73) Assignee: State of Israel, Ministry of Agriculture & Rural Development, Agricultural Research Organization, Bet Dagan (IL)

( * ) Notice: Subject to any disclaimer, the term of this patent is extended or adjusted under 35 U.S.C. 154(b) by 0 days.

(21) Appl. No.: 12/589,687

(22) Filed: Oct. 27, 2009

(65) Prior Publication Data

US 2010/0107287 P1 Apr. 29, 2010

(51) Int. Cl.
*A01H 5/00* (2006.01)

(52) U.S. Cl. ..... Plt./155

(58) Field of Classification Search ..... Plt./155
See application file for complete search history.

*Primary Examiner* — Kent L Bell
(74) *Attorney, Agent, or Firm* — Foley & Lardner LLP

(57) ABSTRACT

A new and distinct almond variety of *Prunus dulcis* named 'MATAN', particularly characterized by self-fertility and production of high quality almond fruit with a large kernel.

4 Drawing Sheets

Botanical name of the genus and species of the plant claimed: *Prunus dulcis.*

Variety denomination: 'MATAN'.

This application claims priority under 35 U.S.C. § 119(f) of the Israeli Plant Breeder's Rights Application No. 4169/08 filed Oct. 29, 2008.

BACKGROUND OF THE INVENTION

The present invention relates to a new and distinct variety of almond tree, botanically known as *Prunus dulcis,* synonymous with *Prunus amygdalus* Batsch., *Amygdalus communis* L., and *Amygdalus dulcis* Mill., belongs to the Rosaceae family, and is hereinafter referred to by the variety denomination 'MATAN'.

The new *Prunus dulcis* 'MATAN' is a product of a controlled breeding program conducted by the inventors, Doron Holland, Irit Bar-Ya'akov, Kamel Hatib and Reuven Birger in the Yizre'el Valley, Israel. The objective of the breeding program was to develop a new *Prunus dulcis* variety which is self fertile and produces almond fruit, of high quality and with a large kernel.

The new *Prunus dulcis* 'MATAN' originated from a cross made by the inventors in 2001 in Yizre'el Valley, Israel. The female or seed parent is the French, self-fertile *Prunus dulcis* variety designated Lauranne, (unpatented), and the male or pollen parent is the local *Prunus dulcis* variety designated 'Um El Fahem' (unpatented). The new *Prunus dulcis* 'MATAN' was selected by the inventors from the progeny of the stated cross in a controlled environment in 2005 in Yizre'el Valley, Israel.

Asexual propagation of the new *Prunus dulcis* 'MATAN' by grafting onto the *Prunus persica* (*L.*) *Batsch*×*Prunus amygdalus batsch*) rootstock designated GF.677 (unpatented), was first performed in March of 2005 (two trees) and then in February of 2006 (six trees) in the orchard located in Yizre'el Valley, Israel. Asexual propagation of the new *Prunus dulcis* 'MATAN' has demonstrated that the combination of characteristics as herein disclosed for the new variety is firmly fixed and retained through successive generations of asexual propagation. The new variety reproduces true-to-type.

BRIEF DESCRIPTION OF THE INVENTION

The following traits have been repeatedly observed and are determined to be unique characteristics of 'MATAN' which in combination distinguish this almond tree as a new, unique and distinct variety:

1. self-fertility;
2. production of high quality almond fruit; and
3. large kernel of almond fruit.

In comparison to the parental varieties, 'Lauranne' (unpatented) and 'Um El Fahem' (unpatented), 'MATAN' differs primarily in the traits listed in Table 1.

TABLE 1

Comparison with parent varieties.

| Trait | New Variety 'MATAN' | Female Parent 'Lauranne' (unpatented) | Male Parent 'Um El Fahem' (unpatented) |
|---|---|---|---|
| Self-fertility | Present | Present | Absent |
| Beginning of Flowering | February | March | February |
| Time of Ripening | July | August | July |
| Dry Fruit shell | Semi-Hard, Breakable | Hard, Complete | Soft |
| Taste | Sweet | Slightly Bitter | Sweet |

Among the many commercial varieties known to the present inventors, the variety most similar to 'MATAN' is the female parent, 'Laurane', as described in the foregoing Table 1.

BRIEF DESCRIPTION OF THE PHOTOGRAPHS

The accompanying photographs illustrate the overall appearance of the new *Prunus dulcis* 'MATAN' showing the colors as true as is reasonably possible with colored reproductions of this type. Colors in the photographs may differ slightly from the color values cited in the detailed morphological description, which accurately describe the color of 'MATAN'.

FIG. 1, taken in 2009, shows a profile of a fruit-bearing, four-year-old, tree of 'MATAN'.

FIG. 2, taken in 2006, shows a close-up view of a fruit-bearing, four-year-old, tree of 'MATAN'.

DETAILED MORPHOLOGICAL DESCRIPTION

Figure 1:
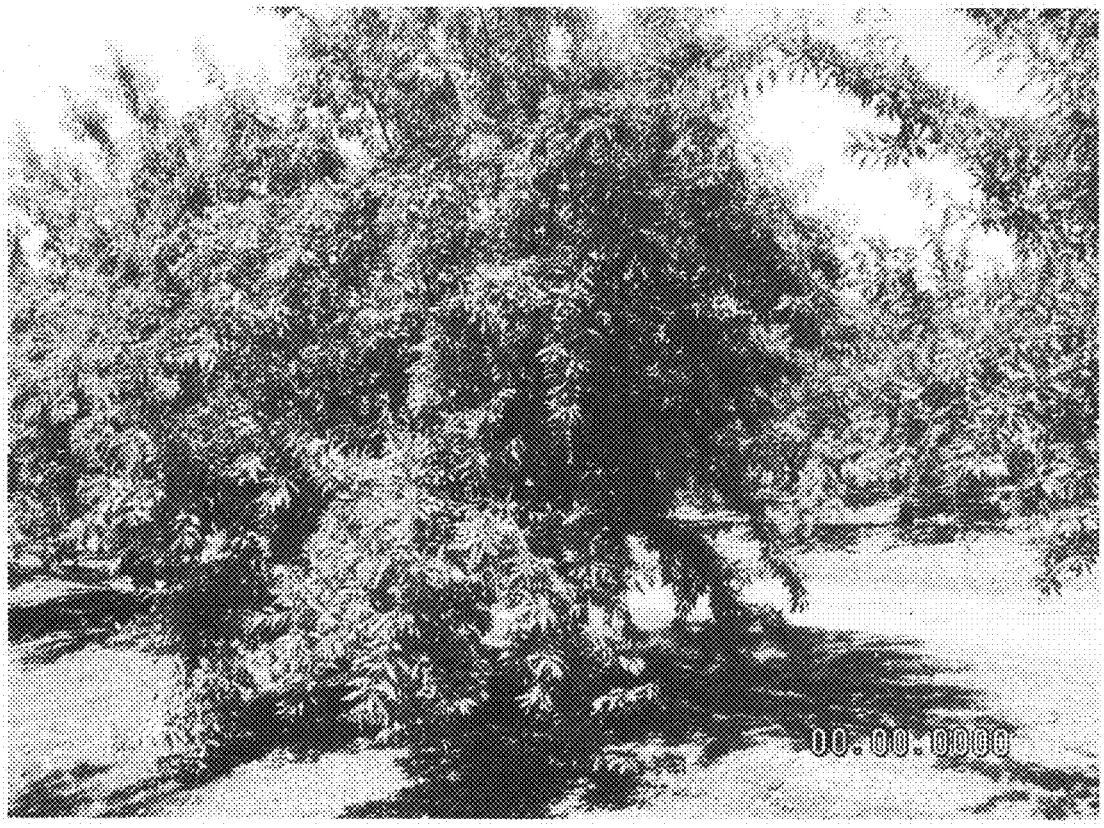
Figure 2:
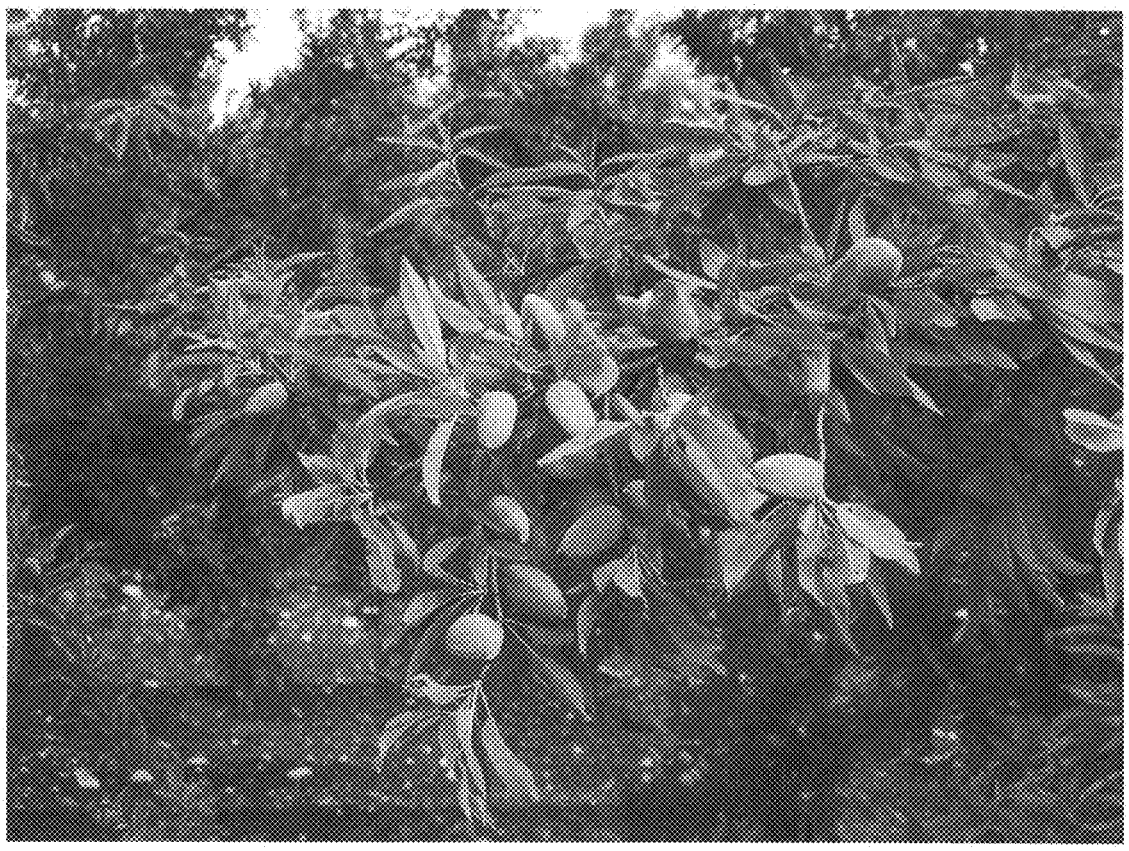
Figure 3:
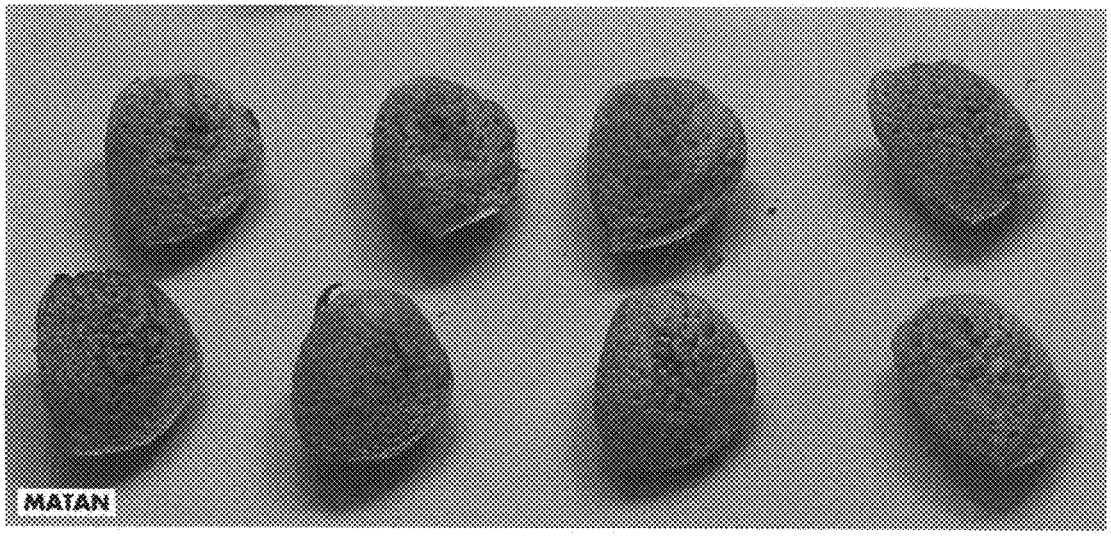
FIG. 3 shows different close-up images of typical dry fruit of 'MATAN'.
Figure 4:
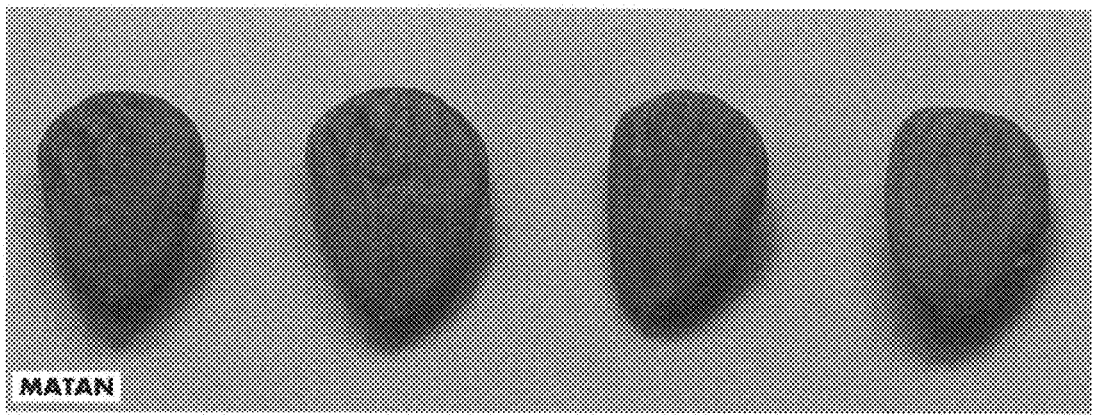
FIG. 4 shows different close-up images of typical kernels of mature fruit of 'MATAN'.

The new *Prunus dulcis* 'MATAN' has not been observed under all possible environmental conditions. The phenotype of the new variety may vary with variations in environment such as temperature, light intensity, and day length without any change in the genotype of the almond tree.

The aforementioned photographs, together with the following observations, measurements and values describe trees of 'MATAN' as grown in Yizre'el Valley, Israel, in an open orchard under conditions which closely approximate those generally used in commercial practice. The trees of 'MATAN' were planted mainly in clay grumusol (vertisol) soil at an elevation of about 100 meter above sea level, at latitude 32°42'N, longitude 35°11'E. Yizre'el Valley is characterized by a Mediterranean subtropical climate, with an average annual rainfall of about 580 mm concentrated from November through March. Mean diurnal minimum temperature in January is 6° C. (43° F.), and mean diurnal maximum temperature in July is 33° C. (91° F.). Fertilization of about 250 kg/ha N and 300 kg/ha K is administered per year.

Unless otherwise stated, the detailed morphological description includes observations, measurements and values based on four-year-old 'MATAN' trees grown in the Yizre'el Valley, Israel from 2006 to 2009. Quantified measurements are expressed as an average of measurements taken from a number of trees of 'MATAN'. The measurements of any individual tree, or any group of trees, of the new variety may vary from the stated average.

Color references are made to The Royal Horticultural Society Colour Chart (R.H.S.), 1986 edition, except where general colors of ordinary significance are used. Color values were taken under conditions of full sunlight.

All of the trees of 'MATAN', insofar as they have been observed, have been consistent in all the characteristics described below.

Classification:

*Botanical.*—*Prunus dulcis.*

Parentage:

*Female or seed parent.*—*Prunus dulcis* 'Lauranne' (unpatented).

*Male or pollen parent.*—*Prunus dulcis* 'Um El Fahem' (unpatented)

Propagation: Grafting onto unpatented (*Prunus persica*×*Prunus amygdalus*) rootstock designated GF.677.

Growing conditions:

*Light intensities.*—Full sunlight.

*Temperature.*—Mean diurnal minimum temperature in January is 6° C. (43° F.), and mean diurnal maximum temperature in July is 33° C. (91° F.).

*Fertilization.*—About 250 kg/ha N and 300 kg/ha K is administered per year.

*Growth regulators.*—No growth regulators are used.

Table of characteristics:

*Tree.*—Time of leaf bud burst: end of February. Vigor: strong. General shape (canopy): upright, moderately spreading. Habit: a medium-sized tree with one trunk and 4 and 5 main branches; main branches spreading; crown symmetrical and round in shape. Branching habit: main branches angle is 30° to 60° with respect to trunk when allowed to grow naturally. Type of bearing: fruit set on branches mainly on distal part of branch. Height: about 4.5 m. Diameter of crown: about 12 m. Density of foliage: Dense. Number of main branches per tree: 3 or 4 resulting from pruning. Length of main branches: varies; maximum of about 4 m; minimum of about 3 m. on average, branches grow about 50 cm to 60 cm per growing season, new branchlets form, radiating from the older, primary branch.

*Trunk.*—Diameter of trunk: 43-45 cm (rootstock). Color of bark: greyed brown. Surface of bark: semi rough. Lenticels length: 1.5 to 2.5 cm. Lenticels width: about 0.5 cm. Lenticels density: medium. Lenticels shape: elonged. Lenticels color: grey RHS 201 A.

*Current season shoot.*—Shape in cross section: round. Length: up to 1.5 m. Thickness: 24 mm. Color: green RHS 146 B. Anthocyanin coloration: present on sunny side. Intensity of anthocyanin coloration: medium.

*One-year-old shoot.*—Shape in cross section: round. Length: up to 2 m. Thickness: 0.51 cm. Color: green RHS 146 D. Anthocyanin coloration: present, between RHS 178 B and RHS 178 C. Intensity of anthocyanin coloration: strong. Feathering: none. Pubescence: glabrous. Lenticels: none. Spur: present.

*Spur.*—Number: 1-4 on 20 cm of shoot. Length: 5-11 mm. Thickness: 1-3 mm. Color: green RHS 146 D. Anthocyanin coloration: present, between RHS 178 B and RHS 178 C. Intensity of anthocyanin coloration: strong. Surface: smooth.

*Foliage.*—Density: medium-dense.

*Leaf blade.*—Length: 90-100 mm. Width: 20-30 mm. Length/width ratio: small. Shape: narrow ovate. Shape of base: right angle Shape of Apex: acute. Green color upper side: medium green RHS 147 A. Green color lowest side: gray green RHS 137 B. Undulation of margin: very weak. Incisions of margin: crenate. Depth of incision: 1 mm. Shape in cross section: straight. Venation type: pinnate venation from central vein to the leaf edge. Prominence of main vein on lower side: strong. Color of main vein on lower side: medium gray green RHS 137 C.

*Petiole.*—Length: 19-20 mm. Thickness: 1-2 mm. Color of upper side: medium gray green RHS 137 C. Color of lower side: gray green RHS 138 B. Cross section: slightly concave.

*Flower buds.*—Distribution: rarely on spurs.

*Flower bud.*—Shape: elliptical. Length: 8-9 mm. Diameter: 3-4 mm. Color: dark brown RHS 200 B. Hairiness: covered with white hairs RHS 155 C. Attitude towards shoot: held out. Color of tip of petals: white pink RHS 56 D, fades away with development.

*Vegetative bud.*—Shape: concical. Length: 3-4 mm. Diameter: 2-3 mm. Color: dark brown RHS 200 B.

Hairiness: covered with white hairs RHS 155 C. Attitude towards shoot: adpressed. Time of development of vegetative bud: after flowering.

*Flower.*—Type: flowers are born single or clustered with 2 or 3 per cluster mainly on branches rarely on spurs. Diameter: 28-35 mm. Number of stamen: numerous. Number of pistils: one. Position of stigma compared with anthers: at level or slightly above. Fragrance: none or very slight.

*Petal.*—Number of petals: five. Shape: broad elliptic. Shape of apex: rounded. Shape of tip: indented. Depth of incision of tip: 1-2 mm. Shape of base: nearly right angle with tiny claw. Length: 16-21 mm. Width: 10-15 mm. Undulation of margin: medium. Margin: entire. Color of upper side: white RHS 155 D. Color of lower side: white RHS 155 D with pink blush RHS 65 D.

*Sepal.*—Number of sepals per flower: five. Shape: broad elliptic. Length: 3-4 mm. Width: 3-4 mm. Shape of apex: rounded. Margin: entire Color of outer side: grayish green between RHS 138 A and RHS 138 B with strong anthocyanin coloration RHS 184 B. Color of inner side: green RHS 145 B sometimes with medium anthocyanin coloration RHS 184 B. Internal color at base: dark orange RHS 28 B. Hairiness: medium strong.

*Stamen.*—Filament length: 4-7 mm. Filament color: white RHS 155 A with purple RHS 183 D. Anthocyanin coloration of filament: present. Anther size: minuscule. Pollen color; yellow RHS 5 B.

*Style.*—Style length: 9-11 mm. Style color: yellowish green RHS 149 C. Style hairiness: strong. Style Hairs color: white.

*Stigma.*—Size: very small. Color: yellowish green RHS 149 C.

*Ovary.*—Shape: cylindrical. Pubescence: very Strong.

*Green fruit.*—Type: drupe. Length: 45-50 mm. Width: 30-35 mm Thickness of exocarp: 3-4 mm. Color of outer side: gray green RHS 147 D. Color of inner side: light Green RHS 145 C. Shape: elongated. Shape of apex: right angle. Shape of base: truncate. Pubescence: strong. Surface: smooth velvety. Color of pubescence: very light green RHS 145 D. Time of maturity: beginning of August.

*Dry fruit.*—Shape: elongated. Weight: 6.5-7.5 g. Length: 37-45 mm Width: 24-28 mm. Thickness: 15-20 mm. Color: beige RHS 164 C. Surface: with residue of exocarp. Shape of apex: right angle with mucron. Thickness of endocarp: thin. Resistance of cracking: weak. Left-over of hull (residue of exocarp on dry fruit): Present. Keel development: strong. Splitting: absent.

*Fruit.*—Percentage of double kernels: none. Eating quality: excellent. Keeping quality: dried fruit and nuts can be stored for over 1 year. Maturity when described: ripe for eating. Maturity period: beginning of August in Yizre'el Valley. Date of first and last picking (harvest): about August 1st and August 15th in Newe Yaar, Israel. Distribution on tree: well distributed throughout.

*Kernel.*—Shape: ovate. Size: large. Weight: 1.6 g. Length: 25-30 mm. Width: 14-17 mm. Thickness: 6-7 mm. Main color: brown red RHS 164 A. Rugosity: medium rough. Taste: sweet.

*Time of beginning of flowering.*—End of January.

*Flowering period.*—Up to 10 days depending on weather conditions.

*Cropping behavior.*—Harvest starts and ends during the first 2 weeks of August in Yizre'el Valley, Israel.

*Production per year.*—Fruit production depends on fruit set which depends on prevailing weather conditions, and subsequent development of fruit.

Market: Food market.

Disease/pest resistance: No atypical resistance has been noted.

Disease/pest susceptibility: No atypical resistance has been noted.

Winter hardiness: Tolerant to temperatures down −9° C. without observed damage to wood and buds of dormant almond trees.

Drought/heat tolerance: Tolerant to temperatures up to 33° C., growth is limited by drought periods without irrigation.

What is claimed is:

1. A new and distinct variety of almond tree of *Prunus dulcis* named 'MATAN', as illustrated and described herein.

* * * * *